US012678031B2

(12) United States Patent (10) Patent No.: US 12,678,031 B2
Jensen et al. (45) Date of Patent: Jul. 14, 2026

(54) ENDOSCOPE HAVING A STEERING WIRE ACTUATOR

(71) Applicant: AMBU A/S, Ballerup (DK)

(72) Inventors: Thomas Bachgaard Jensen, Værløse (DK); Irene Rivas Palacios, Copenhagen (DK); Michael Kappler Hansen, Vallensbæk (DK)

(73) Assignee: AMBU A/S, Ballerup (DK)

( * ) Notice: Subject to any disclaimer, the term of this patent is extended or adjusted under 35 U.S.C. 154(b) by 193 days.

(21) Appl. No.: 18/615,777

(22) Filed: Mar. 25, 2024

(65) Prior Publication Data

US 2024/0324861 A1 Oct. 3, 2024

(30) Foreign Application Priority Data

Mar. 27, 2023 (EP) .................................... 23164282

(51) Int. Cl.
*A61B 1/005* (2006.01)
*A61B 1/00* (2006.01)
*A61M 25/01* (2006.01)

(52) U.S. Cl.
CPC ........ *A61B 1/0052* (2013.01); *A61B 1/00128* (2013.01); *A61B 1/0057* (2013.01); *A61M 25/0136* (2013.01); *A61M 25/0147* (2013.01)

(58) Field of Classification Search
CPC . A61B 1/0052; A61B 1/00128; A61B 1/0057; A61B 1/00042; A61B 1/0011; A61B 1/0055; A61M 25/0136; A61M 25/0147
See application file for complete search history.

(56) References Cited

U.S. PATENT DOCUMENTS

| | | | |
|---|---|---|---|
| 4,203,430 | A | 5/1980 | Takahashi |
| 5,383,852 | A | 1/1995 | Stevens-Wright et al. |
| 5,462,527 | A | 10/1995 | Stevens-Wright et al. |
| 5,480,203 | A | 1/1996 | Favalora et al. |
| 5,752,912 | A | 5/1998 | Takahashi et al. |
| 5,888,192 | A | 3/1999 | Heimberger |

(Continued)

FOREIGN PATENT DOCUMENTS

| | | |
|---|---|---|
| EP | 1046406 A2 | 10/2000 |
| JP | 2005013613 A | 1/2005 |

(Continued)

OTHER PUBLICATIONS

Extended European search report issued in European Application No. 23164282.8, mailed Sep. 7, 2023, 7 pages.

*Primary Examiner* — Amit Chatly
(74) *Attorney, Agent, or Firm* — Faegre Drinker Biddle & Reath LLP

(57) ABSTRACT

An endoscope (1) including: an insertion cord (3) including a bending section (20); a handle (2) comprising a steering wire actuator (60); and a first steering wire (27) and a second steering wire (28) both connected to the steering wire actuator (60) and running through the insertion cord (3) so that manipulation of the steering wire actuator (60) causes bending of the bending section (20); the steering wire actuator (60) including: a first fixing structure (62) including a first hook (30) for fixation of a first steering wire (27) closed loop, a second fixing structure including a second hook (31) for fixation of a second steering wire (28) closed loop.

24 Claims, 7 Drawing Sheets

(56) References Cited

U.S. PATENT DOCUMENTS

| | | | |
|---|---|---|---|
| 5,938,588 | A | 8/1999 | Grabover et al. |
| 7,285,088 | B2 | 10/2007 | Miyake |
| 8,790,250 | B2 | 7/2014 | Petersen et al. |
| 9,678,275 | B1 | 6/2017 | Griffin |
| 10,165,931 | B2 | 1/2019 | Petersen et al. |
| 10,321,804 | B2 | 6/2019 | Jacobsen et al. |
| 10,617,284 | B2 | 4/2020 | Matthison-Hansen |
| 10,624,531 | B2 | 4/2020 | Matthison-Hansen |
| 10,624,617 | B2 | 4/2020 | Matthison-Hansen et al. |
| 10,631,716 | B2 | 4/2020 | Matthison-Hansen |
| 10,779,710 | B2 | 9/2020 | Matthison-Hansen |
| 11,166,627 | B2 | 11/2021 | Hansen et al. |
| 11,291,355 | B2 | 4/2022 | Lund et al. |
| 11,357,392 | B2 | 6/2022 | Matthison-Hansen et al. |
| 11,478,135 | B2 | 10/2022 | Matthison-Hansen |
| 2001/0023313 | A1 | 9/2001 | Ide |
| 2001/0041891 | A1 | 11/2001 | Thompson et al. |
| 2002/0164130 | A1 | 11/2002 | Elkins, II et al. |
| 2004/0199052 | A1 | 10/2004 | Banik et al. |
| 2005/0107667 | A1 | 5/2005 | Danitz et al. |
| 2006/0111209 | A1 | 5/2006 | Hinman et al. |
| 2006/0200047 | A1 | 9/2006 | Galdonik et al. |
| 2007/0282167 | A1 | 12/2007 | Barenboym et al. |
| 2008/0249483 | A1 | 10/2008 | Slenker et al. |
| 2010/0069834 | A1 | 3/2010 | Schultz |
| 2010/0280320 | A1 | 11/2010 | Alvarez et al. |
| 2010/0280525 | A1 | 11/2010 | Alvarez et al. |
| 2011/0054287 | A1 | 3/2011 | Schultz |
| 2013/0190561 | A1 | 7/2013 | Oskin et al. |
| 2014/0251042 | A1 | 9/2014 | Asselin et al. |
| 2014/0257240 | A1 | 9/2014 | Burdulis |
| 2014/0336573 | A1 | 11/2014 | Yu et al. |
| 2015/0366435 | A1 | 12/2015 | Williams |
| 2016/0100771 | A1 | 4/2016 | Chiba |
| 2017/0252025 | A1 | 9/2017 | Cabiri et al. |
| 2018/0207401 | A1 | 7/2018 | Wang |
| 2018/0296069 | A1* | 10/2018 | Matthison-Hansen ..................... A61B 1/0057 |
| 2018/0309908 | A1 | 10/2018 | Matthison-Hansen et al. |
| 2020/0229684 | A1* | 7/2020 | Lund ................... A61B 1/0052 |
| 2020/0312546 | A1 | 10/2020 | Matsumoto et al. |
| 2021/0338052 | A1 | 11/2021 | OuYang et al. |
| 2022/0061634 | A1 | 3/2022 | Thissen et al. |
| 2022/0167836 | A1 | 6/2022 | Thissen et al. |
| 2023/0404375 | A1 | 12/2023 | Jensen et al. |

FOREIGN PATENT DOCUMENTS

| | | | |
|---|---|---|---|
| KR | 101224305 | B1 | 1/2013 |
| WO | 2022062513 | A1 | 3/2022 |
| WO | 2023226538 | A1 | 11/2023 |

* cited by examiner

ENDOSCOPE HAVING A STEERING WIRE ACTUATOR

CROSS-REFERENCE TO RELATED APPLICATIONS

This application claims priority from and the benefit of European Patent Application No. EP 23164282.8, filed Mar. 27, 2023; the disclosure of said application is incorporated by reference herein in its entirety.

TECHNICAL FIELD

The present disclosure relates to an endoscope and a method for assembling the endoscope. More particularly, the disclosure relates to a bending section with a steering wire actuator operable to bend a bending section of the endoscope.

BACKGROUND

Flexible endoscopes for medical purposes are often provided with a bending section at a distal end of an insertion tube. This enables the user of the endoscope to maneuver the distal tip of the endoscope inside the human anatomy, such as in the airways, in the kidneys or the gastro-intestinal system, and e.g., to study or perform procedures at tissue of interest. The bending section is typically bent by pulling steering wires. If the endoscope is a 2-way bending endoscope, i.e., bending in two opposite directions but in the same plane, the bending section will typically be controlled by two steering wires, which are controlled by one steering wire actuator arranged in the handle of the endoscope, allowing the user to bend the bending section by adjusting a bending lever. If the endoscope is a four-way bending endoscope, i.e., also bending in two opposite directions in a second plane perpendicular to the first mentioned plane, the bending section will typically be controlled by four steering wires, where one steering wire actuator controls two steering wires for bending in the first plane, and the other steering wire actuator controls the two other steering wires for bending in the second plane. Typically, each steering wire actuator is controlled by a rotational wheel on the endoscope handle.

During manufacturing and assembly of an endoscope, the steering wires need to be connected both to the distal end of the bending section and to the steering wire actuator in the handle. This is typically done manually, and when attaching the steering wires to the steering wire actuator the steering wires are inserted through small holes and the tension on both steering wires for bending in one plane needs to be adjusted to an optimal level, where both too much hysteresis and too much friction in the bending is avoided, and so that the bending section is straight when the steering wire actuator is in a neutral position. The steering wire actuator may comprise a roller rotatably mounted in the handle of the endoscope. During use of the endoscope rotation of the roller in one direction may pull one steering wire and loosen one steering wire, and thereby bend the bending section to one side.

The threading of the steering wires through small holes on the steering wire actuator is often difficult and time consuming. Improvements are desirable to reduce manufacturing and assembly costs, particularly for single-use endoscopes.

SUMMARY

It is an object of the present disclosure to provide an endoscope where especially the time and reliability of the assembly process can be improved. Thus, in one embodiment of the present disclosure according with a first aspect, an endoscope comprises a first fixing structure including a first hook for fixation of a first steering wire closed loop and a second fixing structure including a second hook for fixation of a second steering wire closed loop.

The first steering wire closed loop may be formed with a first steering wire free end and the second steering wire closed loop may be formed with a second steering wire free end. Alternatively, both closed loops may be formed with free ends of a steering wire that extends to the tip of the endoscope and back. In general, a steering wire closed loop may be formed by bending a steering wire free end approximately 180 degrees back to the steering wire itself. It can be kept in this position e.g., while attaching the closed loop to the first or second hook, and e.g., while adjusting the tension on the steering wire. The term "closed loop" may be understood such that for a steering wire free end bent back to the steering wire itself, the steering wire free end will be close to the steering wire itself for example by touching or having a small distance e.g., less than 1 mm.

The advantage of the present embodiment is that the assembly process for this endoscope can be faster and easier, partly because there will be no small holes on the steering wire actuator through which the steering wires need to be threaded. This also means that it will be faster to train new people working on the assembly line for this process. Alternatively, it may also be simpler to automate this part of the assembly process.

A hook may here have any shape allowing a loop of a steering wire to be attached to it so that the hook may act on the steering wire with a pulling force. The attachment of a steering wire, such as a free end of a steering wire, to itself after having formed a loop, may for example be done by crimping, gluing, or welding.

The attachment of a free end of a steering wire to itself may take place after the formed loop has been attached to the hook. The attachment of a free end of a steering wire to itself may also take place after the tension of the steering wire has been adjusted to a predetermined value for the endoscope. The value of the tension will depend on several other parameters of the endoscope.

The endoscope according to the present embodiment may also comprise an insertion cord including a bending section; a handle or interface comprising a steering wire actuator; the first steering wire free end and the second steering wire free end, both connected to the steering wire actuator and running through the insertion cord so that manipulation of the steering wire actuator causes bending of the bending section.

The first steering wire closed loop is looping around the first fixing structure by the first steering wire free end turning around and back to the first steering wire to which it is attached. The second steering wire closed loop is looping around the second fixing structure by the second steering wire free end turning around and back to the second steering wire to which it is attached. In a variation, or an alternative, the first steering wire closed loop can be formed by looping the first steering wire free end around the first fixing structure and back, and the second steering wire closed loop can be formed by looping the second steering wire free end around the second fixing structure and back.

In a variation of the present embodiment, the steering wire actuator comprises a first wire drum curved surface and a second wire drum curved surface. The first wire drum curved surface is configured for supporting the first steering wire when the steering wire actuator is moved to pull the first steering wire and the second wire drum curved surface is configured for supporting the second steering wire when the steering wire actuator is moved to pull the second steering wire. The application of curved or, preferably, circular arc surfaces, has the advantage that a rotational movement of the steering wire actuator can result in a maximum displacement of the steering wire compared to only moving the fixing structure where the steering wire is fixated.

In a variation of the present embodiment, the first and second wire drum curved surfaces and the first and second hook are arranged on a roller being arranged inside the handle, configured to enable rotational movements in relation to a center axis. Also, in this variation the first and second wire drum curved surfaces, the first and second hook and the roller may be made in a single piece of polymer material. The advantage being that the roller including hooks and wire drums can be assembled as one part into shells forming the endoscope handle. Further, manufacturing this part by injection molding will be a cost effective and reliable process.

In a variation of the present embodiment, guiding walls are arranged at the first and second wire drum curved surfaces thereby forming a first groove and a second groove in which the first and second steering wires are placed, respectively. The forming of grooves provides a stable design to mitigate the risk that the steering wire could be accidentally removed from the wire drum during manipulation of the steering wire actuator or roller.

In a variation of the present embodiment, the roller comprises a first plate having a first surface on which the first hook is arranged and a second plate having a second surface on which the second hook is arranged, the first and second surfaces being arranged in two different, but substantially parallel or parallel, planes displaced by a distance d, where d is preferably in the range 2-7 mm. One advantage of this displacement between the two plates is that it ensures that the two steering wires will not get into contact between the roller and a part where they are introduced into wire pipes guiding the steering wires through the insertion cord. Another advantage is, that this displacement makes it possible to have more space for other components in the part of the handle where the roller is placed. By substantially parallel it is meant that the first and second planes are angled with respect to each other by no more than 30 degrees, preferably less than 20 degrees, and even more preferably less than 10 degrees, whereas when the first and second planes are parallel they are angled at 0 degrees to each other.

In a variation of the present embodiment, both the first and the second hook comprises a base part extending from the first and second surfaces, respectively, and a holding part extending from the base part, where the holding part may extend in parallel with, or substantially in parallel with, the first and second surfaces, respectively. Also, in this variation each of the first and second plates may be provided with a hole at the positions where the holding parts of the first and second hooks are projected on the first and second surfaces, respectively. This has the advantage that the roller including the hooks may be simpler to mold, e.g., by injection molding.

In a variation of the present embodiment, each of the holes in the roller plates, where the hooks are projected on the surfaces, covers a larger area than the area of the corresponding projected holding part. This makes it easier to arrange the loop of the steering wire into the hook, e.g., by a pair of tweezers, or another tool.

In a variation of the present embodiment, the base parts of the hooks each comprises a receiving surface for supporting the steering wire closed loop, the receiving surface being provided with a curvature having a radius of at least 1 mm, preferably at least 1.5 mm, where a part of the looping steering wire follows this curvature. An advantage of this is when adjusting the tension on the steering wires in manufacturing. In this adjustment the steering wire is pulled with a force providing the desired tension to the steering wire. The steering wire will slide on the receiving surface until the tension is achieved. This sliding will be smoother when the receiving surface has the radius of at least 1 mm, as compared to a receiving surface having sharper edges or corners. Therefore, a more precise adjustment of the tension on a steering wire may be possible. The radius of the receiving surface could alternatively be in the interval 1 mm to 8 mm, preferably 1.5 mm to 6 mm. This would provide similar advantages.

In a variation of the present embodiment, a supporting pin is arranged on the first surface between the first hook and the first wire drum curved surface, and a further supporting pin is arranged on the second surface between the second hook and the second wire drum curved surface, the supporting pins being configured to limit displacement of the first and the second steering wire in a radial direction away from the center axis of the roller. An advantage of this supporting pin is to prevent accidental removal of the steering wire from the wire drum during manipulation of the steering wire actuator or roller.

In a variation of the present embodiment, wherein rotation of the roller is controllable by a bending lever connected to the roller and extending to an external side of the handle, where the bending lever is attached to the roller by a snap fit. This facilitates a simple assembly process.

In a variation of the present embodiment, the holding part of the hook is provided with a barb portion for preventing unintentional removal of the steering wire loop from the hook. This facilitates a more reliable design considerably reducing any risk of the steering wire being unintentionally removed from the hook.

In a variation of the present embodiment, the looping of the steering wire around the hook is the only fixation of the steering wire to the steering wire actuator. This also facilitates a simple assembly process.

In a second aspect the disclosure relates to a method for assembling an endoscope, the method comprising the steps of:

providing a handle part and a steering wire actuator arranged inside the handle part such that rotational movement of the roller is enabled, the roller having a first hook and a second hook, providing a first and a second steering wire partly inserted into wire pipes, providing two handle parts, securing wire pipes in a wire pipe fastener connected to the first handle part, fixating a steering wire actuator in a neutral position, adjusting the bending section to a non-bent position, forming a loop of a free end of the first steering wire, arranging the loop to the first hook, adjusting the tension on the first steering wire, and then attaching the free end of the first steering wire to the first steering wire, forming a loop of a free end of the second steering wire, arranging the loop to the second hook, adjusting the tension on the second steering wire, and then attaching the free end of the second steering wire to the second steering wire.

This assembly method has the advantage of being performed without having to thread steering wires through small holes in steering wire fixing structures. The method is therefore faster and simpler.

In a third aspect the disclosure relates to a system comprising an endoscope according to the first aspect and variations thereof, a monitor and a control unit.

BRIEF DESCRIPTION OF THE FIGURES

The above-mentioned embodiments and variations, features and advantages thereof will be further elucidated by the following illustrative and nonlimiting detailed description of embodiments disclosed herein with reference to the appended drawings, wherein.

Figure 1:
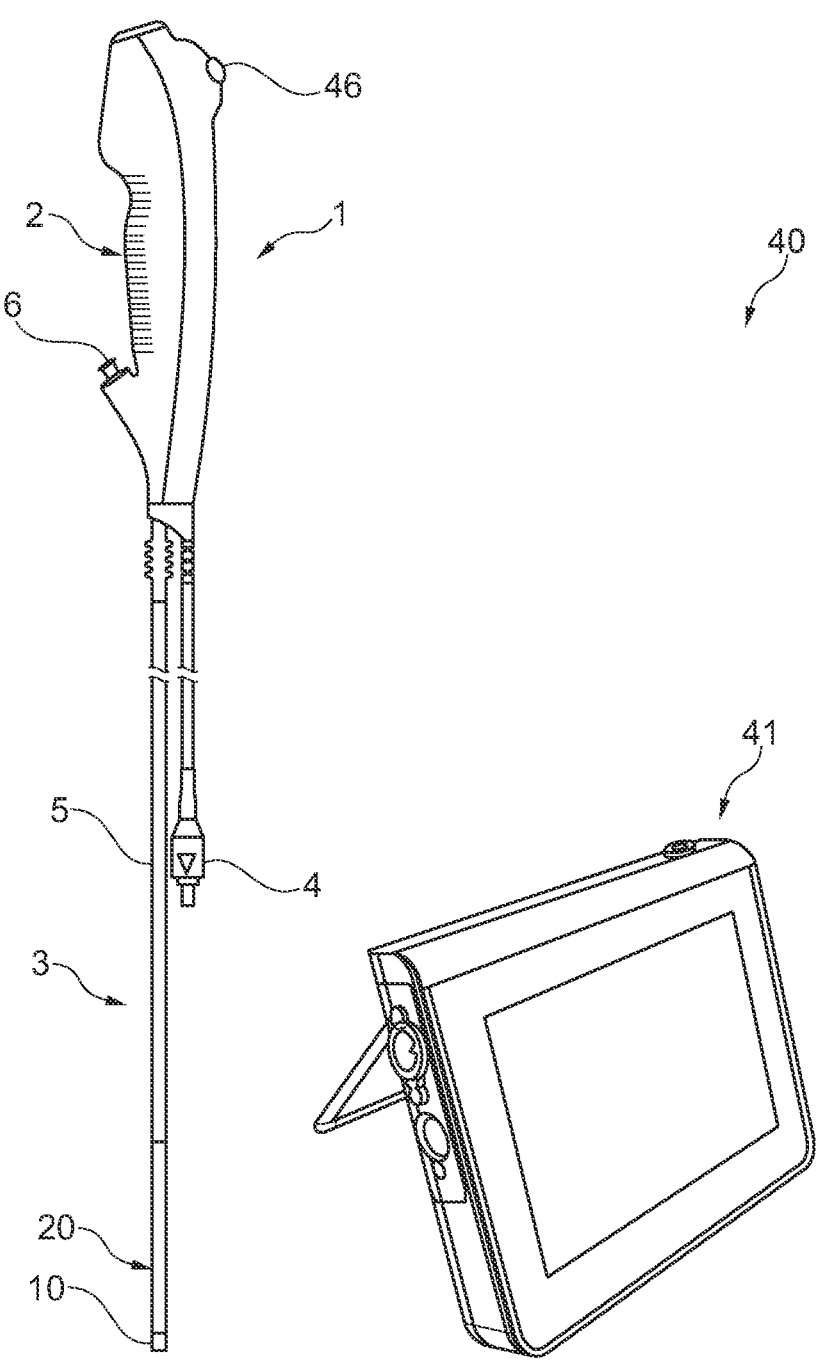
FIG. 1 shows an endoscope and a monitor with a control unit.

In the drawings, corresponding reference characters indicate corresponding parts, functions, and features throughout the several views. The drawings are not necessarily to scale and certain features may be exaggerated in order to better illustrate and explain the disclosed embodiments. For simplicity, this disclosure will focus on a two-way bending endoscope, but the disclosure is relevant for, and covers, also a four-way bending endoscope.

DETAILED DESCRIPTION

In the following description, for purposes of explanation, specific details are set forth in order to provide an understanding of the invention. It will be apparent, however, to one skilled in the art that the invention can be practiced without all these details. Furthermore, one skilled in the art will recognize that embodiments of the present invention, described below, may be implemented in a variety of ways, such as a process, an apparatus, a system, a device, or a method on a tangible computer-readable medium.

Connections between components or systems within the figures are not intended to be limited to direct connections. The terms "coupled," or "connected" shall be understood to include direct connections and indirect connections through one or more intermediary devices or components.

Furthermore, (1) certain steps may optionally be performed; (2) steps may not be limited to the specific order set forth herein; (3) certain steps may be performed in different orders; and (4) certain steps may be done concurrently.

The disclosure(s) of the following U.S. patent(s) are incorporated herein by reference in their entirety: U.S. Pat. No. 11,291,355.

FIG. 1 illustrates an endoscope 1, which comprises a handle 2, an insertion cord 3 and an electrical cable with a connector 4 for connecting the endoscope 1 to a monitor 41. The insertion cord 3 is the part to be inserted into a body lumen during an endoscopic procedure. The insertion cord comprises a distal tip 10, a bending section 20 and a main tube 5. The handle 2 may comprise an entrance to a working channel 6 running through the insertion cord to the distal tip. The handle also comprises a bending lever 46, which can be used for bending the bending section.

The distal tip 10 comprises a camera and light emitters, e.g., in the form of one or more LEDs or the end of an optical light fiber.

The monitor 41 may comprise an electronic circuit for receiving and processing the image stream from the camera as well as a processor for image processing, user interface, storage of images etc. But the monitor part and the electronic circuit and processor part may also be separate parts. The electronic circuit and the processor part are also referred to as a control unit. A visualization system, or system 40, may comprise the endoscope 1 and the monitor 41.

Figure 2:
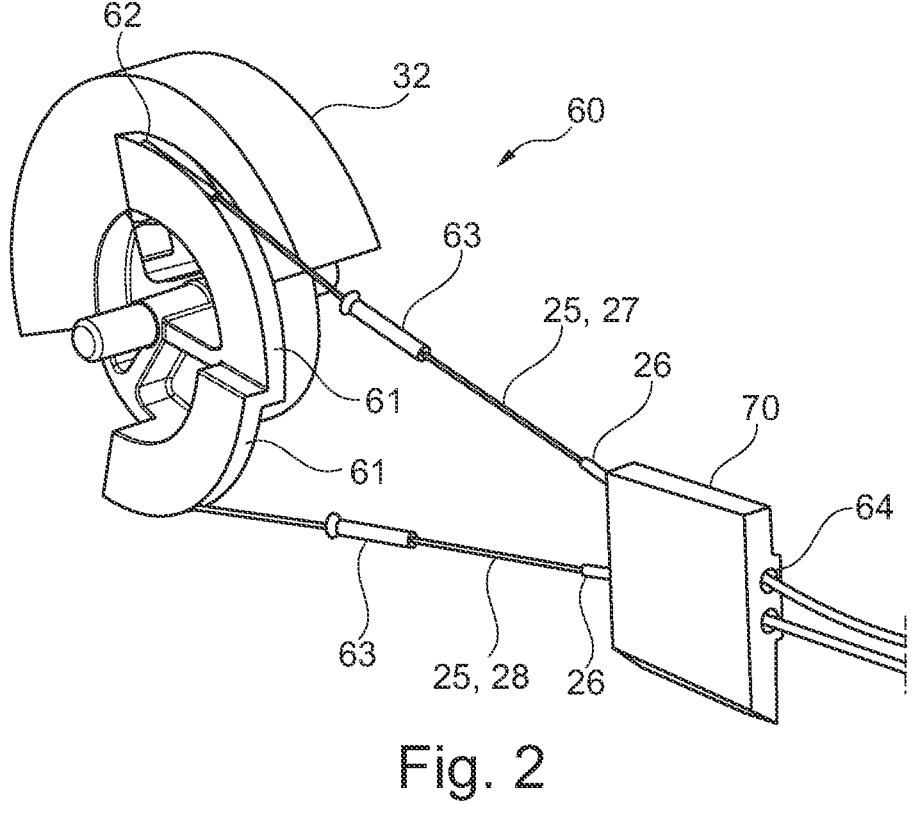
FIG. 2 shows an example of a steering wire actuator, here in the form of a roller, and a wire pipe fastener.

FIG. 2 shows a schematic example of a roller 32 for a steering wire actuator 60 configured for bending the bending section by pulling the proximal, free, ends 25 of steering wires 27 and 28. The steering wires 27, 28 are moved by rotation of wire drum curved surfaces 61, which are circular arc surfaces or curved surfaces placed on a roller 32 and supporting the steering wires. In the example one end of the steering wire has been drawn through a fixing structure 62 and bent back and fastened to itself by a crimp 63. The steering wires are surrounded in part by wire pipes 26. The system shown in FIG. 2 works for a two-way bending endoscope. For a four-way bending endoscope two independently rotatable wire drums are typically applied.

FIG. 2 further shows the wire pipe fastener 70 into which the wire pipes 26 are may be fixated e.g., by gluing in a glue passage 64. The wire pipe fastener is secured inside the handle, optionally directly to a handle shell. The distal ends of the wire pipes 26 may be fixated and terminated at the proximal end of the bending section 20.

Figure 3:
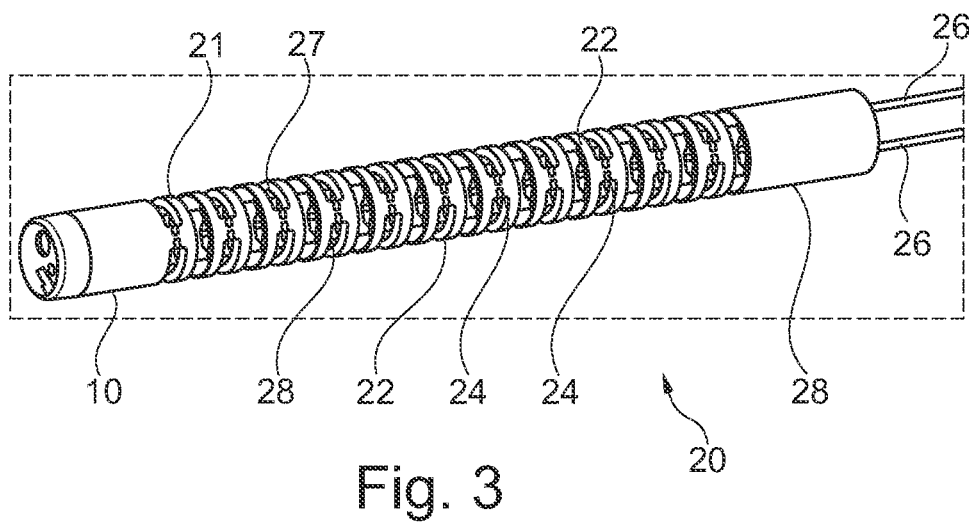
FIG. 3 shows a distal end of an endoscope including a bending section.

FIG. 3 shows a distal end of the insertion cord 3 of the endoscope 1, where the bending cover (not shown) typically covering the bending section 20, and often making it watertight, has been removed. The bending section 20 is attached to the main tube 30 in the proximal end and to the distal tip housing 11 in the distal end. In this example the bending section is molded in one piece and comprises a number of segments including a proximal end segment 23, a distal end segment 21, and intermediate segments 22. The segments are held together by hinges 24, so that the segments can be bent relative to each other by manipulation of the steering wires 25. Alternatively, the bending section 20 could be extruded in a relatively soft and resilient material, e.g., a foam-like material, with lumens for steering wires, electrical wires and the tubes passing through. The steering wires 27, 28 are connected in a fixed connection to the distal end, e.g., the distal end bending segment 21. I.e., the steering wire is preferably not movable in relation to the distal end bending segment. Between the handle and the proximal end bending segment 23 the steering wire 27, 28 is guided in the wire pipe 26, which is secured to the wire pipe fastener 70 placed in the handle 2 distal to the steering wire actuator 60 (see FIG. 2). Other designs of the bending section are also possible.

Figure 4A:
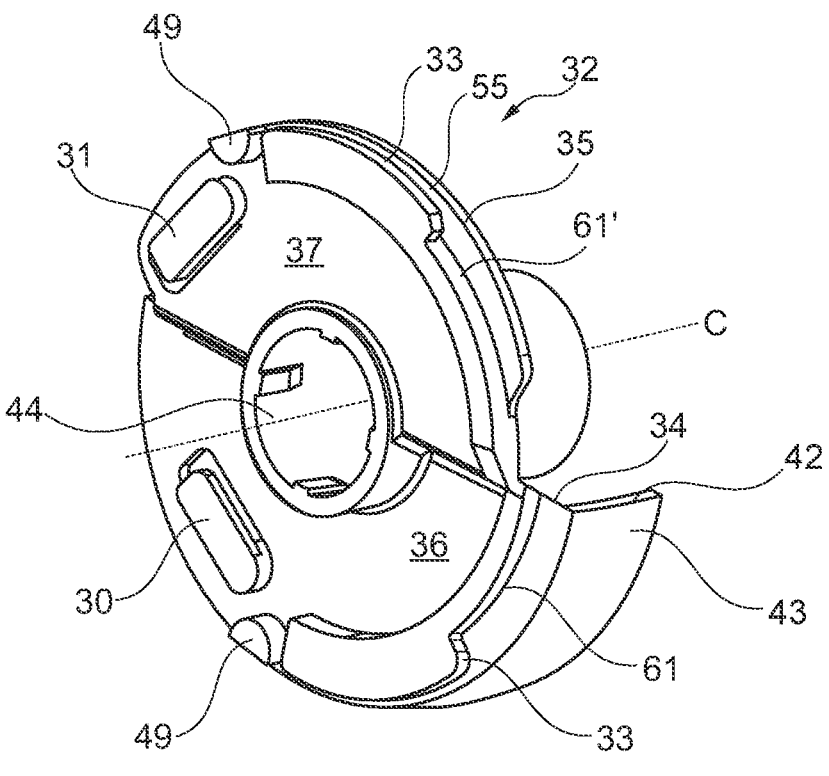
FIGS. 4A, 4B and 4C show a variation of a steering wire actuator in the form of a roller with two hooks.
Figure 4B:
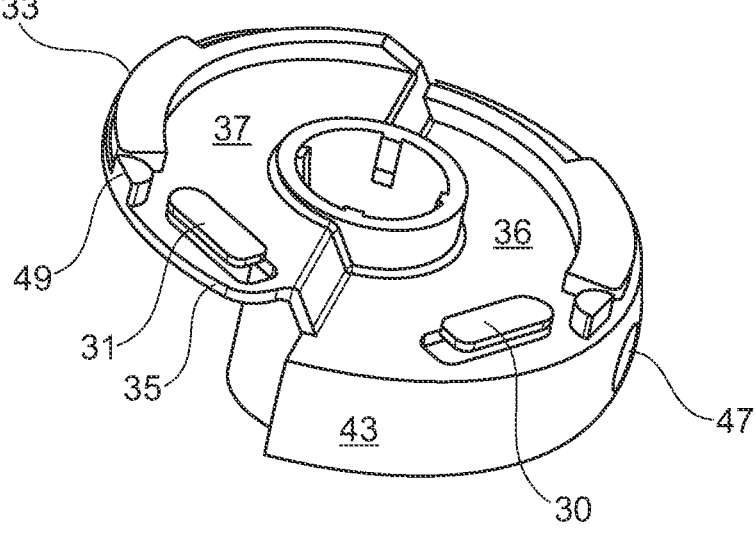
Figure 4C:
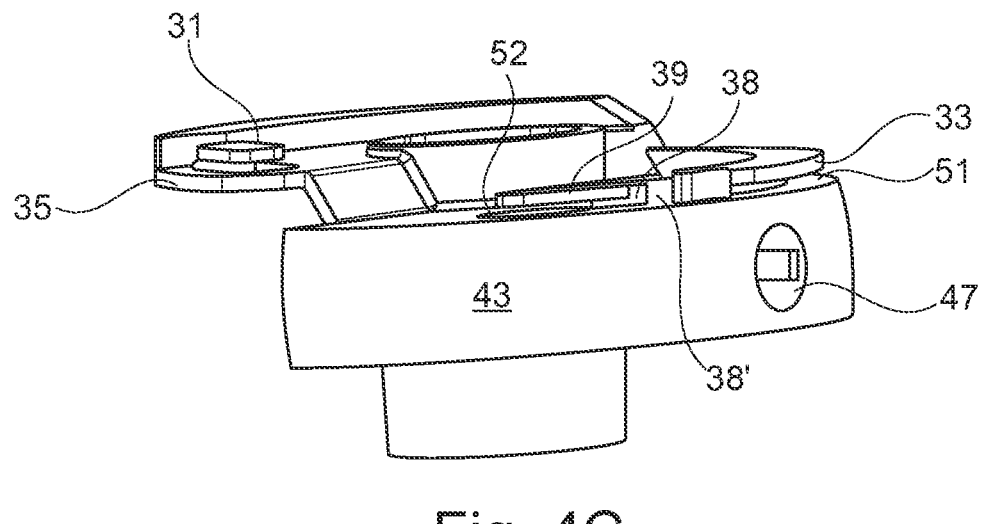

FIGS. 4A-C show a variation of a roller 32 of the steering wire actuator 60. The roller 32 comprises a passage 44 for a shaft 45 (see FIG. 8) on which the roller is arranged such that it can be rotated to some extent when the bending lever 46 is manipulated. This rotation is preferably around the center axis c. The bending lever 46 is attached in a fixation hole 47 and should extend to the external side of the handle 2. The bending lever 46 may pass through a slit in the handle 2. The slit can be dimensioned so that the bending lever can be moved while rotating the roller. To avoid an open access to the inside of the handle 2, an arcuate cover surface 43 on the roller 32 forms part of an arcuate wall 42 and is preferably placed in a slidable abutment to the edge of the slit on the inside of the handle. The arcuate wall 42 may extend in parallel to the center axis c.

The roller 32 is prepared for controlling the pulling of a first and a second steering wires 27, 28 by having a first hook 30 for attachment of a loop formed by an end section of the first steering wire 27, and a second hook 31 for attachment of a loop formed by an end section of the second steering wire 28. End sections of the first steering wire and the second steering wire are preferably not connected in the handle. The first and second steering wires extend through the insertion cord to a fixed connection to the distal end of the insertion cord, at the segment 21 of the bending section 20 or to the tip housing. The roller may be injection molded in one part from a polymer material, such as for example POM, PP or HDPE.

For this disclosure one steering wire is counted as one passage from the steering wire actuator to the distal end of the bending section. I.e. if the same unbroken steering wire continues from the distal end of the bending section and back to the steering wire actuator, and one part is applied for bending, for example, to one side and the other is applied for bending to the opposite side, this is counted as two steering wires, e.g. first and second steering wires 27, 28. Also, when distal wire ends are not attached to each other but each is connected to the distal end of the bending section or the tip part, this is also counted as two steering wires, e.g., first and second steering wires.

The roller 32 may comprise a first plate 34 having a first surface 36 on which the first hook 30 is arranged and a second plate 35 having a second surface 37 on which the second hook 31 is arranged. The first and second plates 34, 35 may be arranged in two different, but parallel or substantially parallel, planes displaced, or offset, by a distance d, where d is preferably in the range 2-7 mm, and more preferably in the range 3-5 mm. Preferably, there will be a similar displacement between the first and second surfaces 36, 37.

The displacement between the first and second surfaces 36, 37 ensures that if the steering wires cross between the roller and the wire pipe fastener 70, they will not rub against each other when manipulating the roller 32 to bend the bending section 20. Furthermore, the first plate 34 of the roller may be limited by the positioning of the attached arcuate cover surface 43, which may be aligned with the slit in the handle 2 for the bending lever 46. The second plate 35 of the roller may, however, be displaced to a position leaving space for other parts inside the handle, for example suctioning tube or valves. However, the maximum rotation of the roller may limit how much space such other parts can use without conflicting with the first plate 34 of the roller and the arcuate cover surface 43 during rotation of the roller 32.

As seen in FIGS. 4A-4C, the wire drum curved surface 61 for the first steering wire 27 is arranged to extend perpendicular from the first surface 36, and the wire drum curved surface 61' for the second steering wire 28 is arranged to extend perpendicular from the second surface 37.

Also, the wire drum curved surfaces 61, 61' are placed close to the periphery of the first and second plates 34, 35 of the roller 32, but so that the peripheral part of the plates 34, 35 may function as a supportive wall for guiding the steering wires 27, 28 when placed on the wire drum curved surfaces

61, 61'. In other words, the first and second plates 34, 35 may extend radially outwardly further than the wire drum curved surfaces 61, 61' to aid in the threading of the wires and to keep the wires from slipping off the wire drum curved surfaces 61, 61'. Further to this, the wire drums may be provided with a further supportive guiding wall 33, at least along a part of the wire drum curved surfaces 61, 61'. This guiding wall should be placed opposite to the first and second plates 34, 35, respectively, thereby forming a groove like passage 51 for the steering wire 27, 28.

There may be some distance between the wire drum curved surfaces 61, 61' and the corresponding hook 30, 31 on the first and second surfaces 36, 37, respectively. A support pin 49 may extend from the first and second surfaces 36, 37 between the wire drum curved surfaces 61, 61' and the corresponding hook 30, 31. This support pin 49 may prevent that the steering wire 27, 28 is unintentionally removed from the groove 51 during rotational movements of the roller 32 for bending of the bending section. These movements imply that the steering wires 27, 28 are alternately pulled and loosened. When a steering wire is loosened, it should not be possible for it to leave or slip out of the groove 51. Such removal can be prevented by the support pin 49, when the steering wire 27, 28 passes the support pin 49 on the side pointing towards a center of the roller (the radially inwardly facing side). The center of the roller may be similar to a center axis c passing through the passage 44 for a shaft 45 for the roller 32.

Figure 5A:
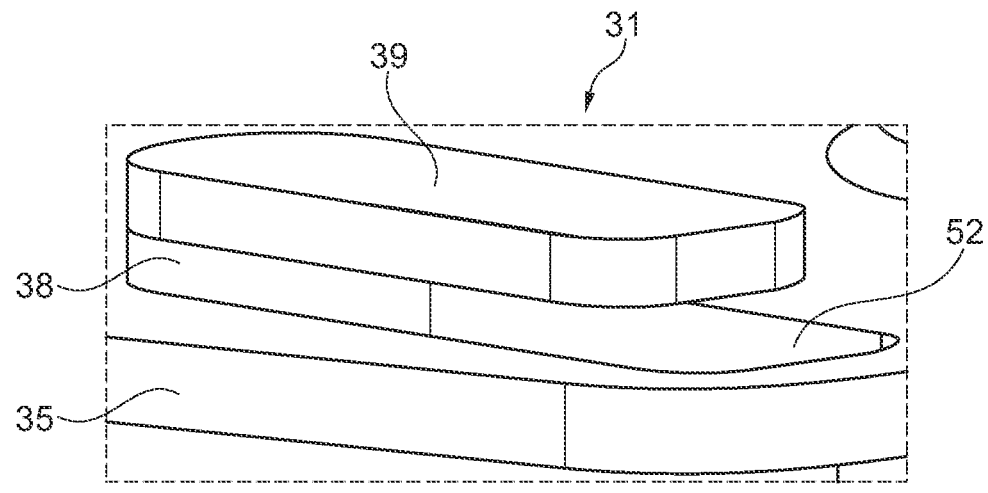
FIGS. 5A and 5B show close-ups of an example of a hook.
Figure 5B:
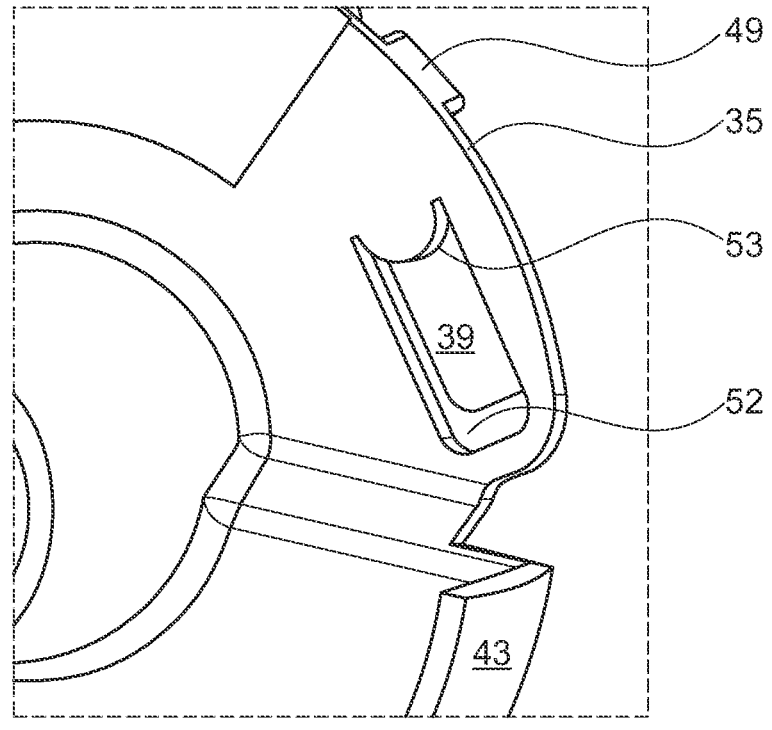

FIGS. 4C and 5A show that the hook 30, 31 may comprise a base part 38 extending perpendicular to the first or second surface 36, 37 of the roller. The hook further comprises a holding part 39 extending from the base part 38 in parallel with, or substantially in parallel with, the first and second surfaces 36, 37 of the roller 32. FIG. 5B shows the hook from the other side of the first or second plate 34, 35 of the roller 32, i.e., the side opposite to the surface 36, 37 from where the base part 38 of the hook is extending. Here, it is seen that the first and second plates 34, 35 may be provided with a hole 52 at the positions where the holding parts 39 of the first and second hooks 30, 31 are projected on the first and second surfaces 36, 37, respectively. One advantage of the hole 52 is that the roller 32 may be designed for a simple one-shot injection molding manufacturing. As seen in FIG. 5B, the hole 52 is also slightly larger than the holding part 39 of the hook 30, 31.

As indicated in FIGS. 5A and 5B, the hole 52 below the holding part 39 of the hook 30, 31 is longer than the holding part 39, when measured from the base part 38 to the point of the hole 52 and of the holding part 39 furthest away from the base part 38. It has been found that this makes it easier to arrange the loop of the steering wire 27, 28 to the hook during manufacturing, as more space will be available for a pair of tweezers to maneuver the loop of the steering wire 27, 28 into position at the hook 30, 31. To achieve this, the hole 52 may be at least 0.5 mm longer than the length of the holding part. The length of the holding part 39 and the hole 52 is measured from the base part 38 and in a direction away from the base part, e.g., the part of the holding part 39 furthest away from the base part. As shown, the holding part 39 extends from the base 38 in a circumferential direction away from the respective guiding wall 61, 61', with a respective support pin 49 between the base and the guiding wall 61, 61'. Additionally, the most inward facing surface of the support pin 49 is radially outward relative to the most inward facing surface of the base 38. Furthermore, the most inward facing surface of the support pin 49 is radially inward relative to the groove 51. A circumferentially extending gap 38' can be seen between the base 38 and the support pin 39. The steering wire passes through this gap 38'.

The base part 38 of the hook 30, 31 each comprises a receiving surface 53 for supporting the closed loop of the steering wire 27, 28. The receiving surface may be provided with a curvature having a radius of at least 1 mm, preferably at least 1.5 mm, where a part of the looping steering wire follows this curved receiving surface 53. The pulling force transferred from the roller 32 to a steering wire 27, 28, is transferred through this curved receiving surface 53. The advantage of having the receiving surface 53 curved is that this makes adjustment of the steering wire easier during assembly of the endoscope. Here, the roller is fixated in a neutral position and the bending section is straight, i.e., not bent. A steering wire closed loop is formed and arranged in the hook 30, 31, and the steering wire free end is led back in parallel with the steering wire. In this position of roller, bending section and steering wires, the tension on each steering wire 27, 28 is adjusted to a preselected value before attaching the free end of the steering wire to the same steering wire, e.g. by crimping or gluing.

The tension on each steering wire 27, 28 is adjusted by pulling the free end of the looped steering wire with a well-defined preselected force. Thereby, the steering wire 27, 28 will slide on the receiving surface 53 until a balance with the correct tension on the steering wire is achieved. Attaching the free end of the steering wire to the same steering wire is done while keeping the tension on the steering wire. This procedure is performed for both steering wires.

Figure 6A:
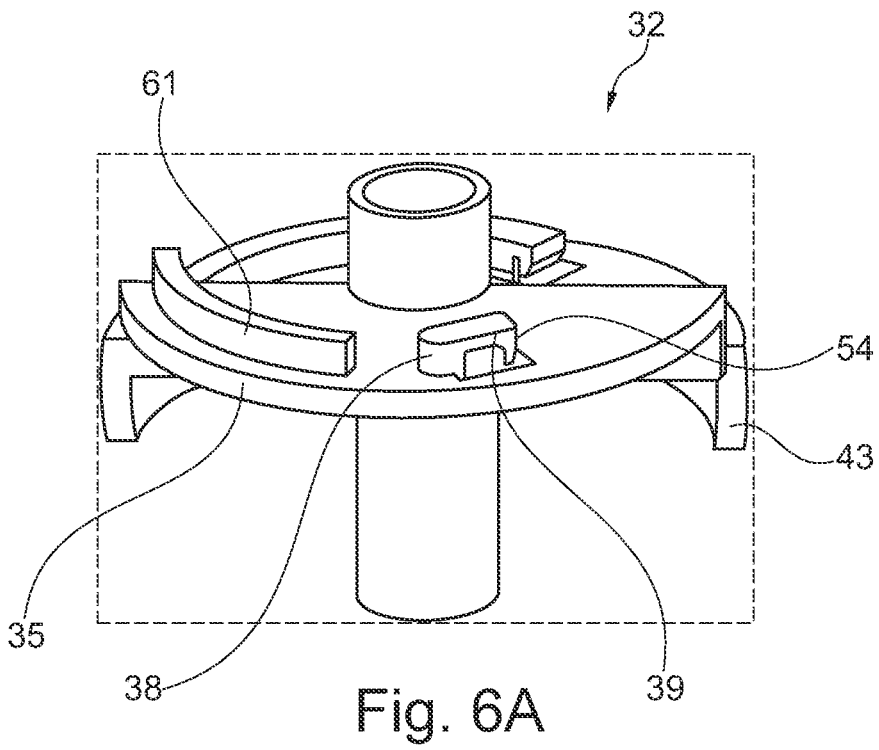
FIGS. 6A and 6B shows another variation of a roller with a hook having a barb.
Figure 6B:
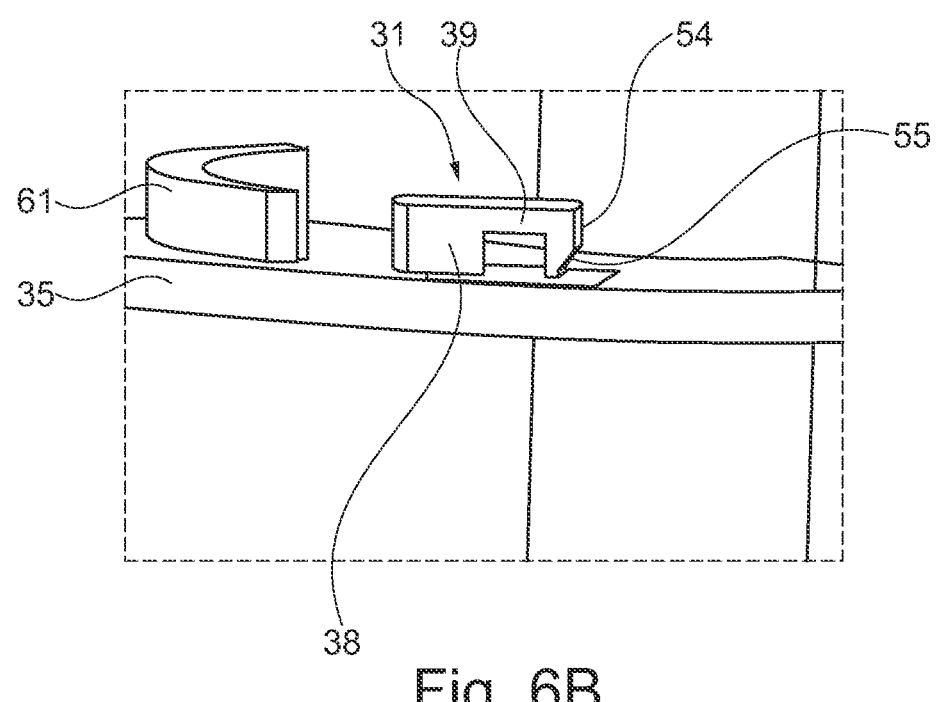

FIGS. 6A and 6B show a variation where the holding part 39 of the hook is provided with a barb 54 for keeping the looped steering wire 27, 28 attached to the hook 30, 31 during manipulation of the roller 32 for bending the bending section 20, during which the steering wire not being pulled may be loosened. The presence of the barb 54 may replace the functionality of the support pin 49 or make the support pin less necessary. Also, the barb 54 may be provided with an inclined surface 55 which may make it easier to arrange the looped steering wire, i.e., the steering wire closed loop in the hook during assembly. The inclined surface extends from the free end of the holding part (the end away from the base) toward the plate and the base. In another example, both the support pin 49 and the barb 54 are provided.

Figure 7:
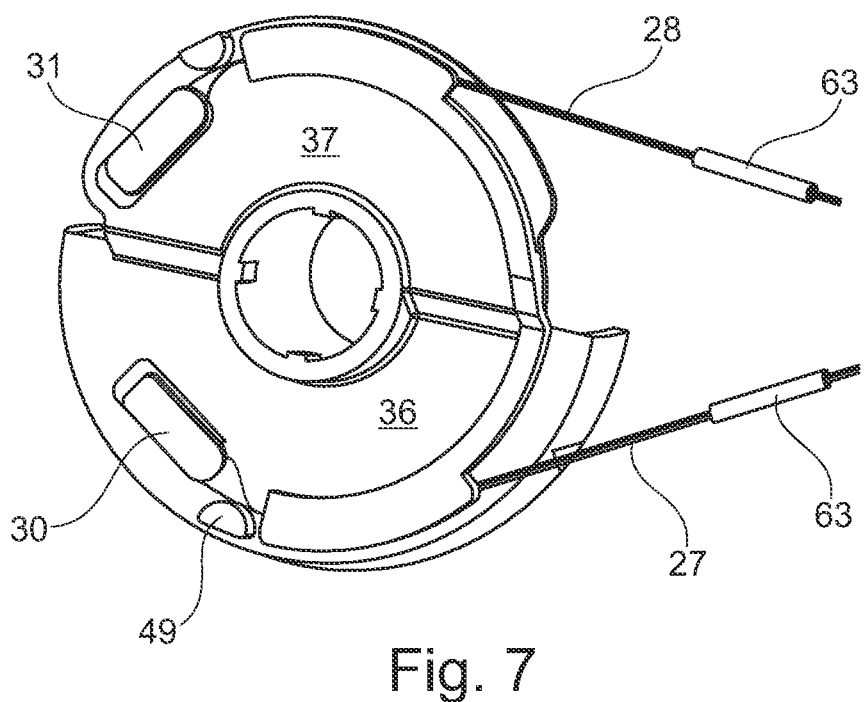
FIG. 7 shows a roller with a hook where steering wires are added.

FIG. 7 shows a roller as in FIGS. 4A-4C, with two steering wires attached. Each steering wire 27, 28 is looping around a separate hook 30, 31, preferably by first forming a closed loop of the steering wire free end, and then attaching the closed loop to the hook by drawing the steering wire in between the holding part 39 of the hook and the corresponding first or second surface 36, 37 of the roller. Each steering wire 27, 28 is attached to itself by application of a crimp 63. Each steering wire is guided in its corresponding groove 51, i.e., the first steering wire is guided on the first surface 36 of the roller 32 by the groove 51 and the support pin 49 and looping around the first hook 30. The second steering wire is guided on the second surface 37 of the roller 32 by the parts on the second surface, i.e., the groove 51 and the support pin 49 and looping around the second hook 31. The steering wires may be made from stainless steel and may have a diameter in the range 0.15-0.35 mm. The proximal ends of the steering wires are looped around the barbed hooks shown in FIGS. 6A and 6B in the same manner.

Figure 8:
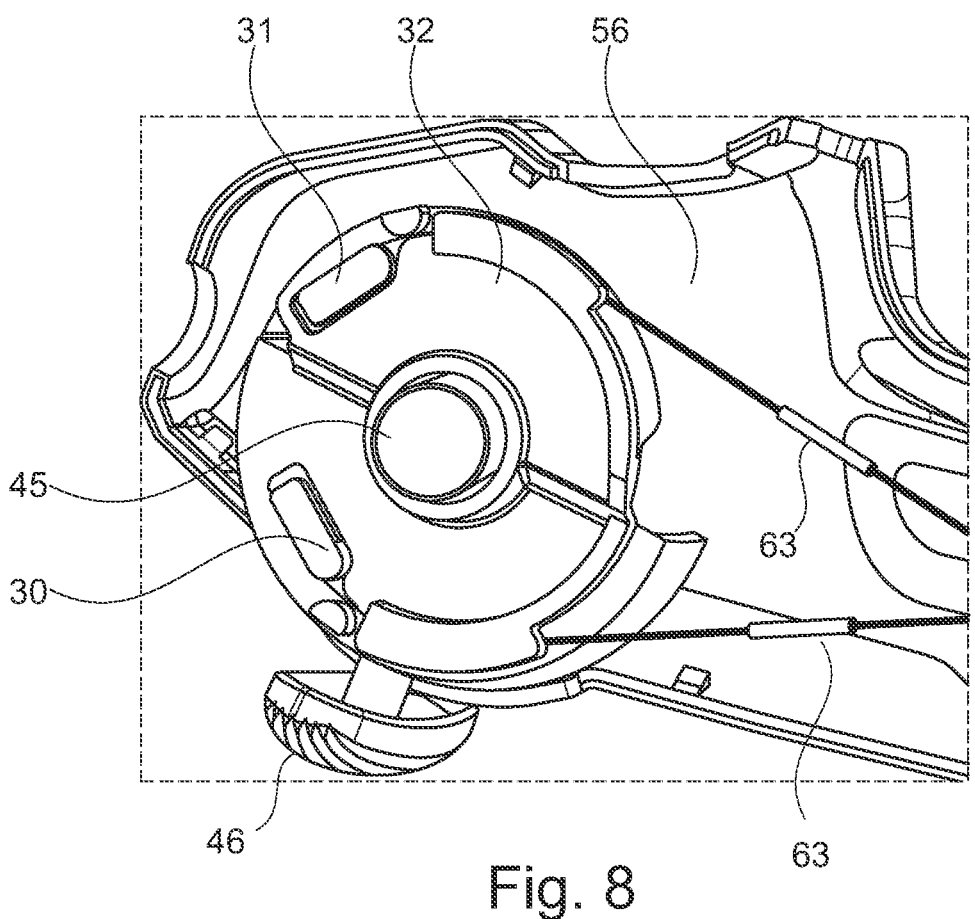
FIG. 8 shows a roller with wire drums and two hooks around which steering wires are looped, placed in one of two handle shells.

FIG. 8 shows one shell part 56 of the handle. This shell part is provided with a shaft 45 for the roller 32. The shaft 45 may be molded as part of the handle shell part 56 but could also be connected to the handle shell part after molding. As seen in FIG. 8, the roller 32 is arranged to the shaft 45 such that the roller can be rotated to some extent by movement of the bending lever 46. This rotational movement will pull one of the steering wires 27, 28, depending on the direction of the rotation, and the other steering wire 27, 28 will be relaxed. In FIG. 8 the steering wires are connected to the roller 32 as shown and described with reference to FIG. 7.

In an example of the roller 32 including the first and second wire drum curved surfaces 61, 61' and the first and second hook 30, 31, an outer diameter of the roller, perpendicular to the center axis c, is 40-45 mm. The passage 44 for a shaft has a diameter of 11-13 mm. The radius of the receiving surface 53 of the base part 38 of the hook is 1.5-2 mm. The holding part 39 of the hook has a length of 7-8 mm and a width of 3.4-3.7 mm. The thickness of the holding part is 0.75-0.9 mm, and the distance between the surface of the roller 36, 37 and the holding part 39 is around 0.6 mm, measured in a direction perpendicular to the surface of the roller. The hole 52 in the surface of the roller below the holding part 39, has a length of 9-10 mm and a width of 3.9-4.2 mm. The area of the holding part 39 of the hook may be 27-30 mm$^2$. The area of the hole 52 below the hook may be 36-40 mm$^2$. The displacement between the first surface of roller 36 and the second surface of roller 37 measured along the center axis c is 3.4-3.6 mm. The thickness of the first and second plates 34, 35 of the roller are 1-1.5 mm.

In this disclosure the handle 2 may be a positioning interface, or interface, which functions to control the position of the insertion cord 3. The handle 2 is an example of a positioning interface and, unless stated otherwise, the terms are used interchangeably. The positioning interface also functions to provide the steering controls, e.g. knobs, levers, buttons, and the like, used to steer the tip of the insertion cord 6, which includes the camera, and the elevator controls. Alternatively, a different positioning interface can be provided that is connected to the insertion cord and is detachably connected to a robotic arm. In a further alternative, the positioning interface is detachably connected to the insertion cord and is therefore reusable. In this example the positioning interface may be affixed to a robotic arm. The insertion cord thus extends from the robotic arm, and the intrusive medical device is detachable from the robotic arm. The robotic arm responds to signals, including voice commands from an operator, to rotate, translate, and otherwise position the proximal end of the insertion cord, as an operator would do manually. The positioning interface can include control actuators, including manual control actuators. Alternatively, or additionally, control actuators can be provided in or on the robotic arm or by the robotic system including the robotic arm, thereby potentially reducing the cost of the intrusive medical device. Example control actuators include single axis actuators, including linear motion actuators. A linear motion actuator may comprise a threaded rod coupled to a threaded nut portion, in which a motor rotates the rod to translate the nut portion.

Single-use endoscopes optimize workflow and reduce cost while saving patient's lives and improving patient care. They optimize workflow and reduce cost because they are always ready when needed without the traditional large-scale capital and repair budgets required for reusable endoscopes. For example, a sterilization and storage facility is avoided, there is no need to maintain evidence of sterilization, and there is no need to transport endoscopes from sterilization and storage facilities to the buildings where they are needed, sometimes in the middle of the night or weekends. They save patient's lives and improve patient care because they are readily available and do not pose a cross-contamination risk. This also reduces hospital re-admissions. While single-use endoscopes are disposed after a single patient use (one or more procedures may be performed while the patient remains in the treatment room), the environmental impact of re-useable endoscopes, due to cleaning materials, $CO_2$ emissions during the cleaning process, and use of disposable personal protective equipment by personnel involved in transportation and sterilization of the re-useable endoscopes, is similar to that of single-use endoscopes. Studies are emerging showing that the environmental impact of single-use endoscopes may, in fact, be less than that of re-usable endoscopes. To further reduce environmental impact, the endoscopes according to the present disclosure are primarily made of polymer materials. Non-polymer materials are typically used for the steering wires, insertion tube or shaft, and electronics components, such as the camera(s), light emitting diodes, circuit boards and components connected to the circuit boards. Endoscopes with elevator bars may include a metal elevator bar wire. The distal tip part may be made, except for the electronic components and wires, exclusively of polymer materials. Metal adapter rings, metal screws, and other non-polymeric components may thus be excluded from the distal tip part. As the focus on reducing environmental impact continues, for example by using polymeric wires as described in commonly owned U.S. Pat. No. 11,291,355, issued on Apr. 5, 2022, the environmental impact of single-use endoscopes will likely continue to shrink.

The following items are further variations and examples of the embodiments described with reference to the figures.

1. An endoscope comprising: an insertion cord including a bending section; a handle comprising a steering wire actuator; a first steering wire and a second steering wire both connected to the steering wire actuator and running through the insertion cord so that manipulation of the steering wire actuator causes bending of the bending section; the steering wire actuator comprising: a first fixing structure including a first hook for fixation of a first steering wire closed loop, a second fixing structure including a second hook for fixation of a second steering wire closed loop.

2. The endoscope according to item 1, wherein the steering wire actuator comprises a first wire drum curved surface and a second wire drum curved surface, the first wire drum curved surface configured for supporting the first steering wire when the steering wire actuator is moved to pull the first steering wire and the second wire drum curved surface configured for supporting the second steering wire when the steering wire actuator is moved to pull the second steering wire.

3. The endoscope according to item 2, wherein the first and second wire drum curved surfaces and the first and second hook are arranged on a roller being arranged inside the handle, configured to enable rotational movements in relation to a center axis.

4. The endoscope according to item 3, wherein the first and second wire drum curved surfaces, the first and second hook and the roller is made in a single piece of polymer material.

5. The endoscope according to item 2, 3 or 4, wherein guiding walls are arranged at the first and second wire drum curved surfaces thereby forming a first groove and a second groove in which the first and second steering wires are placed, respectively.

6. The endoscope according to item 3, 4 or 5, wherein the roller comprises a first plate having a first surface on which the first hook is arranged and a second plate having a second surface on which the second hook is arranged, the first and second surfaces being arranged in two different, but substantially parallel or parallel, planes displaced by a distance d, where d is preferably in the range 2-7 mm.

7. The endoscope according to item 6, wherein both the first and the second hook comprises a base part extending from the first and second surfaces, respectively, and a holding part extending from the base part, where the holding part may extend in parallel with, or substantially in parallel with, the first and second surfaces, respectively.

8. The endoscope according to item 7, wherein each of the first and second plates are provided with a hole at the positions where the holding parts of the first and second hooks are projected on the first and second surfaces, respectively.

9. The endoscope according to item 8, wherein each of the holes covers a larger area than the area of the corresponding projected holding part.

10. The endoscope according to item 7, 8 or 9, wherein each base part comprises a receiving surface for supporting the steering wire closed loop, the receiving surface being provided with a curvature having a radius of at least 1 mm, preferably at least 1.5 mm, where a part of the looping steering wire follows this curvature.

11. The endoscope according to any one of the items 3-10, wherein a supporting pin is arranged on the first surface between the first hook and the first wire drum curved surface, and a further supporting pin is arranged on the second surface between the second hook and the second wire drum curved surface, the supporting pins being configured to limit displacement of the first and the second steering wire in a radial direction away from the center axis of the roller.

12. The endoscope according to any one of the previous items, wherein the holding part of the hook being provided with a barb portion for preventing unintentional removal of the steering wire loop from the hook.

13. The endoscope according to any one of the previous items, wherein the looping of the steering wire around the hook is the only fixation of the steering wire to the steering wire actuator.

14. A method for assembling an endoscope comprising the steps of: providing a handle part and a roller arranged inside the handle part such that rotational movement of the roller is enabled, the roller having a first hook and a second hook, providing a first and a second steering wire partly inserted into wire pipes, providing two handle parts, securing wire pipes in a wire pipe fastener connected to the first handle part, adjusting the roller to a neutral position, adjusting the bending section to a non-bent position, forming a loop of a free end of the first steering wire, arranging the loop to the first hook, adjusting the tension on the first steering wire, and then attaching the free end of the first steering wire to the first steering wire, forming a loop of a free end of the second steering wire, arranging the loop to the second hook, adjusting the tension on the second steering wire, and then attaching the free end of the second steering wire to the second steering wire.

15. A system comprising an endoscope according to any one of items 1-13, a monitor and a control unit.

LIST OF REFERENCES 1 endoscope
2 handle 3 insertion cord
4 electrical cable with plug
5 main tube
6 working channel
10 distal tip
20 bending section
21 distal end segment
22 intermediate segment
23 proximal end segment
24 hinges
25 steering wire
26 wire pipe
27 first steering wire
28 second steering wire
30 first hook
31 second hook
32 roller
33 guiding wall
34 first plate of roller
35 second plate of roller
36 first surface of roller
37 second surface of roller
38 base part of hook
39 holding part of hook
40 system
41 monitor
42 arcuate wall
43 arcuate cover surface
44 passage for a shaft
45 shaft for roller
46 bending lever
47 fixation hole for bending lever
49 support pin
51 groove
52 hole below hook
53 receiving surface
54 barb
55 inclined surface on barb
56 handle shell part
60 steering wire actuator
61, 61' wire drum curved surface
62 fixing structure
63 crimp
64 glue passage
65 control wheel
66 control wheel
70 wire pipe fastener
c center axis

We claim:

1. An endoscope comprising:
an insertion cord including a bending section;
a handle comprising a steering wire actuator;
a first steering wire and a second steering wire both connected to the steering wire actuator and running through the insertion cord so that manipulation of the steering wire actuator causes bending of the bending section;
wherein the steering wire actuator comprises:
    a first wire drum curved surface configured to support the first steering wire when the steering wire actuator is moved to pull the first steering wire,
    a first hook for fixation of a first steering wire loop, the first hook being spaced apart by an angular separation from the first wire drum curved surface, a second wire drum curved surface configured to support the second steering wire when the steering wire actuator is moved to pull the second steering wire, and
    a second hook for fixation of a second steering wire loop, the second hook being spaced apart by an angular separation from the first wire drum curved surface.

2. The endoscope of claim 1, wherein the steering wire actuator comprises a roller, the roller comprising a first plate and a second plate, the first plate comprising a first surface lying on a first plane, the first hook, and a first arcuate groove including the first wire drum curved surface, the second plate comprising a second surface lying on a second plane, the second hook, and a second arcuate groove including the second wire drum curved surface, the second plane being offset from and substantially parallel or parallel with the first plane, wherein the first hook extends from the first surface in a first direction, and wherein the second hook extends from the second surface in the first direction.

3. An endoscope comprising:
an insertion cord including a bending section;
a handle comprising a steering wire actuator;
a first steering wire and a second steering wire both connected to the steering wire actuator and running through the insertion cord so that manipulation of the steering wire actuator causes bending of the bending section,
wherein the steering wire actuator comprises:
    a first hook for fixation of a first steering wire loop, and
    a second hook for fixation of a second steering wire loop,
wherein the first hook and the second hook each comprises a base part and a holding part, the holding part including a base end opposite a free end, the base end being attached to the base part, wherein the free end of the holding part of the second hook comprises a barb extending toward the second surface, and wherein the free end of the holding part of the first hook comprises a barb extending toward the first surface.

4. An endoscope comprising:
an insertion cord including a bending section;
a handle comprising a steering wire actuator;
a first steering wire and a second steering wire both connected to the steering wire actuator and running through the insertion cord so that manipulation of the steering wire actuator causes bending of the bending section,
wherein the steering wire actuator comprises:
    a first hook for fixation of a first steering wire loop,
    a second hook for fixation of a second steering wire loop,
    a first plate comprising the first hook, a first wire drum curved surface, a first support pin and a first surface lying on a first plane,
    a second plate comprising the second hook, a second wire drum curved surface, a second support pin and a second surface lying on a second plane,
wherein the first hook and the second hook each comprises a base part and a holding part, the holding part including a base end opposite a free end, the base end being attached to the base part, and
wherein the first support pin extends from the first surface intermediate the first hook and the first wire drum curved surface, and wherein the second support pin extends from the second surface intermediate the second hook and the second wire drum curved surface.

5. The endoscope of claim 1, wherein the steering wire actuator comprises a roller, wherein the first wire drum curved surface, the second wire drum curved surface, the first hook, and the second hook, are arranged on the roller inside the handle, the roller being configured to rotate in relation to a center axis.

6. The endoscope of claim 5, wherein the first wire drum curved surface, the second wire drum curved surface, the first hook, the second hook, and the roller are made in a single piece of polymer material.

7. The endoscope of claim 1, wherein guiding walls are arranged at the first wire drum curved surface and at the second wire drum curved surface, thereby forming a first groove in which the first steering wire is placed and a second groove in which the second steering wire is placed.

8. An endoscope comprising:
an insertion cord including a bending section;
a handle comprising a steering wire actuator;
a first steering wire and a second steering wire both connected to the steering wire actuator and running through the insertion cord so that manipulation of the steering wire actuator causes bending of the bending section;
wherein the steering wire actuator comprises a roller, the roller including:
a first hook for fixation of a first steering wire loop,
a second hook for fixation of a second steering wire loop,
a first wire drum curved surface configured to support the first steering wire when the steering wire actuator is moved to pull the first steering wire, and
a second wire drum curved surface configured to support the second steering wire when the steering wire actuator is moved to pull the second steering wire,
a first plate having a first surface on which the first hook is arranged and a second plate having a second surface on which the second hook is arranged, the first and the second surfaces being arranged in two different, but substantially parallel or parallel, planes displaced by a distance d, where d is in a range of 2-7 mm.

9. The endoscope of claim 8, wherein the first hook comprises a base part and a holding part, the base part extending from the first surface and the holding part extending from the base part, and wherein the second hook comprises a base part and a holding part, the base part of the second hook extending from the second surface and the holding part extending from the base part of the second hook.

10. The endoscope of claim 9, wherein each of the first plate and the second plate comprise a hole at positions where the holding parts of the first and the second hooks project onto the first and the second surfaces, respectively.

11. The endoscope of claim 10, wherein each of the holes covers a larger area than a projected area of the corresponding holding part.

12. The endoscope of claim 9, wherein each base part comprises a receiving surface for supporting the first steering wire closed loop and the second steering wire closed loop, respectively, the receiving surface comprising a curvature having a radius of at least 1 mm.

13. The endoscope of claim 8, wherein a supporting pin is arranged on the first plate extending from the first surface between the first hook and the first wire drum curved surface, and a second supporting pin is arranged on the second plate extending from the second surface between the second hook and the second wire drum curved surface, the supporting and the second supporting pin being configured to limit displacement of the first steering wire and the second steering wire, respectively, in a radial direction away from a center axis of the roller.

14. The endoscope of claim 8, wherein the holding part of the hook comprises a barb portion for preventing unintentional removal of the steering wire loop from the hook.

15. The endoscope of claim 1, wherein the first and the second steering wire loops looping around the first hook and the second hook, respectively, is the only fixation of the first and the second steering wires to the steering wire actuator.

16. A method for assembling the endoscope of claim 1, the method comprising:
securing wire pipes in a wire pipe fastener connected to a first handle part of the handle,
adjusting the bending section to a non-bent position,
forming a loop of a free end of the first steering wire, arranging the loop to the first hook, adjusting a tension on the first steering wire, and then attaching the free end of the first steering wire to the first steering wire thereby forming the first steering wire loop,
forming a loop of a free end of the second steering wire, arranging the loop to the second hook, adjusting a tension on the second steering wire, and then attaching the free end of the second steering wire to the second steering wire thereby forming the second steering wire loop.

17. The method of claim 16, wherein adjusting the tension on the first steering wire and adjusting the tension on the second steering wire comprises tensioning the first steering wire to a first predetermined tension and tensioning the second steering wire to a second predetermined tension, said tensioning performed before attaching the free end of the second steering wire to the second steering wire and before attaching the free end of the first steering wire to the first steering wire and after arranging the loops to the first hook and second hook, respectively.

18. A system comprising the endoscope of claim 1, a monitor, and a control unit.

19. A method for assembling an endoscope, the method comprising:
providing a handle part,
securing an insertion cord to the handle part, the insertion cord including a bending section,
providing a first and a second steering wire partly inserted into wire pipes,
arranging a steering wire actuator inside the handle part such that rotational movement of the steering wire actuator is enabled, the steering wire actuator comprising:
a first wire drum curved surface configured to support the first steering wire when the steering wire actuator is moved to pull the first steering wire,
a first hook for fixation of a first steering wire loop, the first hook being spaced apart by an angular separation from the first wire drum curved surface,
a second wire drum curved surface configured to support the second steering wire when the steering wire actuator is moved to pull the second steering wire, and
a second hook for fixation of a second steering wire loop, the second hook being spaced apart by an angular separation from the first wire drum curved surface, running the first and the second steering wires through the insertion cord so that manipulation of the steering wire actuator causes bending of the bending section, securing the wire pipes in a wire pipe fastener connected to the first handle part, adjusting the roller to a neutral position, adjusting the bending section to a non-bent position, forming a loop of a free end of the first steering wire, arranging the loop to the first hook, adjusting a tension on the first steering wire, and then attaching the free end of the first steering wire to the first steering wire, and forming a loop of a free end of the second steering wire, arranging the loop to the second hook, adjusting a tension on the second steering wire, and then attaching the free end of the second steering wire to the second steering wire.

20. An endoscope comprising:

an insertion cord including a bending section;

a handle comprising a steering wire actuator;

a first steering wire and a second steering wire both connected to the steering wire actuator and running through the insertion cord so that manipulation of the steering wire actuator causes bending of the bending section;

wherein the steering wire actuator comprises:

a first wire drum curved surface, a second wire drum curved surface, a first hook for fixation of a first steering wire loop, the first hook comprising a base part and a holding part, the holding part including a base end opposite a free end, the base end being attached to the base part, and the free end being oriented away from the first wire drum curved surface with the base end between the free end and the first wire drum curved surface, and a second hook for fixation of a second steering wire loop, the second hook comprising a base part and a holding part, the holding part including a base end opposite a free end, the base end being attached to the base part, and the free end being oriented away from the second wire drum curved surface with the base end between the free end and the second wire drum curved surface.

21. The endoscope of claim 20, wherein the first hook is radially spaced apart from the first wire drum curved surface, and wherein the second hook is radially spaced apart from the second wire drum curved surface.

22. The endoscope of claim 21, wherein the steering wire actuator comprises a first support pin between the first hook and the first wire drum curved surface.

23. The endoscope of claim 20, wherein the free end of the holding part of the first hook comprises a barb.

24. The endoscope of claim 20, wherein the steering wire actuator is configured to rotate about a center axis, and wherein the first hook and the second hook extend in a common direction perpendicular to the center axis.

* * * * *